US00PP20127P2

(12) United States Plant Patent

Visser et al.

(10) Patent No.: US PP20,127 P2

(45) Date of Patent: Jun. 23, 2009

(54) *THUJA* PLANT NAMED 'MIRJAM'

(50) Latin Name: *Thuja occidentalis*
Varietal Denomination: Mirjam

(76) Inventors: Jeroen Visser, Heidereed 2, 8408 HD Lippenhuizen (NZ); Eduard Visser, Bûtewei 12, 8408 HD Lippenhuizen (NZ)

( * ) Notice: Subject to any disclaimer, the term of this patent is extended or adjusted under 35 U.S.C. 154(b) by 0 days.

(21) Appl. No.: 12/069,864

(22) Filed: Feb. 13, 2008

(51) Int. Cl.
*A01H 7/00* (2006.01)

(52) U.S. Cl. ..... Plt./213

(58) Field of Classification Search ..... Plt./213
See application file for complete search history.

(56) References Cited

PUBLICATIONS

European Plant Breeders'Rights application number 2007/0542 filed Mar. 2, 2007, Copy of published information from the Community Plant Variety Office web site attached.

*Primary Examiner*—Susan B McCormick Ewoldt
(74) *Attorney, Agent, or Firm*—Audrey Charles

(57) ABSTRACT

A new and distinct cultivar of *Thuja* plant named 'Mirjam', characterized by its yellow and yellow-green colored summer foliage, light bronze and yellow-green colored winter foliage, and moderately vigorous, globular growth habit.

2 Drawing Sheets

Latin name of genus and species of plant claimed: *Thuja occidentalis*.
Variety denomination: 'Mirjam'.

BACKGROUND OF THE INVENTION

The present invention relates to a new and distinct cultivar of *Thuja* plant botanically known as *Thuja occidentalis* and hereinafter referred to by the cultivar name 'Mirjam'.

The new *Thuja* is a naturally-occurring branch mutation of a selection of *Thuja occidentalis* 'Danica', not patented characterized by its dull green-colored summer foliage and deep bronze-colored winter foliage. The cultivar Mirjam was discovered and selected by the Inventor while transferring a population of plants of the parent selection from a greenhouse to an outdoor nursery in Lippenhuizen, The Netherlands in summer 1997.

Asexual reproduction of the new *Thuja* by softwood cuttings in a controlled environment in Lippenhuizen, The Netherlands since summer 1997, has shown that the unique features of the *Thuja* are stable and reproduced true to type in successive generations.

SUMMARY OF THE INVENTION

The following characteristics of the new cultivar have been repeatedly observed and can be used to distinguish 'Mirjam' as a new and distinct cultivar of *Thuja* plant:

1. Yellow and yellow-green colored summer foliage;
2. Light bronze and yellow-green colored winter foliage; and
3. Moderately vigorous, globular growth habit.

Plants of the new cultivar differ from plants of the parent primarily in summer and winter foliage color.

Of the many commercially available *Thuja* cultivars, the most similar in comparison to the new cultivar is the parent 'Danica', not patented. However, in side by side comparisons, plants of the new cultivar differ from plants of 'Danica' in the following characteristics:

1. Plants of the new cultivar have a summer foliage color different from plants of 'Danica'; and
2. Plants of the new cultivar have a winter foliage color different from plants of 'Danica'.

In addition, plants of the new cultivar can be compared to plants of 'Golden Globe', not patented. Plants of the new cultivar differ from plants of 'Golden Globe' in the following characteristics:

1. Plants of the new cultivar have a summer foliage color different from plants of 'Golden Globe'; and
2. Plants of the new cultivar have a slightly less globular growth habit than plants of 'Golden Globe'.

Further, plants of the new cultivar can be compared to plants of 'Grüne Kugel', not patented.

1. Plants of the new cultivar have a summer foliage color different from plants of 'Grüne Kugel'; and
2. Plants of the new cultivar have a winter foliage color different from plants of 'Grüne Kugel'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Mirjam'. The plants were grown for approximately 7 years in a 5-liter container Lippenhuizen, The Netherlands in an outdoor nursery location.

The photograph on the first sheet is a side view of the overall growth and habit of 'Mirjam'.

The photograph on the second sheet is a close-up view of the winter foliage of 'Mirjam'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in February, 2007 under natural light conditions in Lippenhuizen, The Netherlands when day temperatures ranged from 0° C. to 10° C. and night temperatures ranged from −5° C. to 5° C.

Plants used in the following description were field grown in Lippenhuizen, The Netherlands, in an outdoor nursery in 5-liter containers and under conditions which closely approximate commercial production conditions. The plants were grown for approximately 7 years. Measurements and numerical values represent averages of typical plants.

Botanical classification: *Thuja occidentalis* cultivar 'Mirjam'.

Parentage:

*Parent.*—*Thuja occidentalis* 'Danica'.

Propagation:

*Type cutting.*—Softwood.

*Time to initiate roots during the summer with an average air temperature of* 18° C.— Approximately 45 days.

*Time to produce a rooted cutting during the summer with an average air temperature of* 18° C.—Approximately 150 days.

*Root description.*—Medium thickness, moderately fleshy, and light grayish brown in color.

*Rooting habit.*—Moderately dense and moderately branching.

Plant Description:

*Plant type and use.*—*Thuja occidentalis* is a slow growing coniferous shrub that can be used as a solitary garden plant or grouped as a hedge planting.

*Commercial crop time.*—Approximately 2 years from a rooted cutting to saleable plant.

*Growth habit and general appearance.*—Moderately vigorous, globular growth habit. Growth rate: Approximately 7.5 cm per season for first two seasons.

*Size.*—Height from soil level to top of plant plane: Approximately 33.0 cm. Width: Approximately 31.5 cm.

*Branching habit.*—Lateral branches arise from main stems that grow freely from the base without pinching. Quantity of lateral branches per plant: Approximately 42.

*Lateral branch.*—Appearance: Branches are dull in appearance, rounded, and covered with scale-like leaves. Strength: Strong. Length: Approximately 22.0 cm. Diameter: Approximately 4.0 mm. Length of central internode: Approximately 1.2 cm. Texture: Glabrous. Color of mature stem: Between 199A and 199C, ages to between 200B and 200C.

Foliage Description:

*General description.*—Durability to stress: Very high. Quantity of leaves per lateral branch: Approximately 3,500. Fragrance: When crushed, strong scent typical of species. Form: Simple. Arrangement: Opposite.

*Leaves.*—Aspect: Acute angle to stem, sessile. Shape: Scale-like, oblanceolate. Margin: Entire. Apex: Short apiculate. Base: Cuneate. Venation pattern: Not observable. Length of mature leaf: Approximately 3.5 mm. Width of mature leaf: 1.7 mm. Texture of upper and lower surfaces: Glabrous, moderately glossy. Color of upper and lower surfaces of young winter foliage: Between N144C and N144D with tips of between 164A and 165B and indistinguishable venation. Color of upper and lower surfaces of young summer foliage: Between N144C and N144D with tips of closest to 1B and indistinguishable venation. Color of upper and lower surfaces of mature winter and summer foliage: 144A with indistinguishable venation.

Cone and seed production: Not available, cone and seed production have not been observed.

Disease and pest resistance: Resistance to pathogens and pests common to *Thuja* has not been observed.

Weather tolerance: Plants of the new *Thuja* have been observed to be hardy to USDA zone 6 and tolerate high temperatures to at least 35° C., and to demonstrate very good tolerance to rain and wind effects.

What is claimed is:

1. A new and distinct cultivar of *Thuja* plant named 'Mirjam', substantially as herein shown and described.

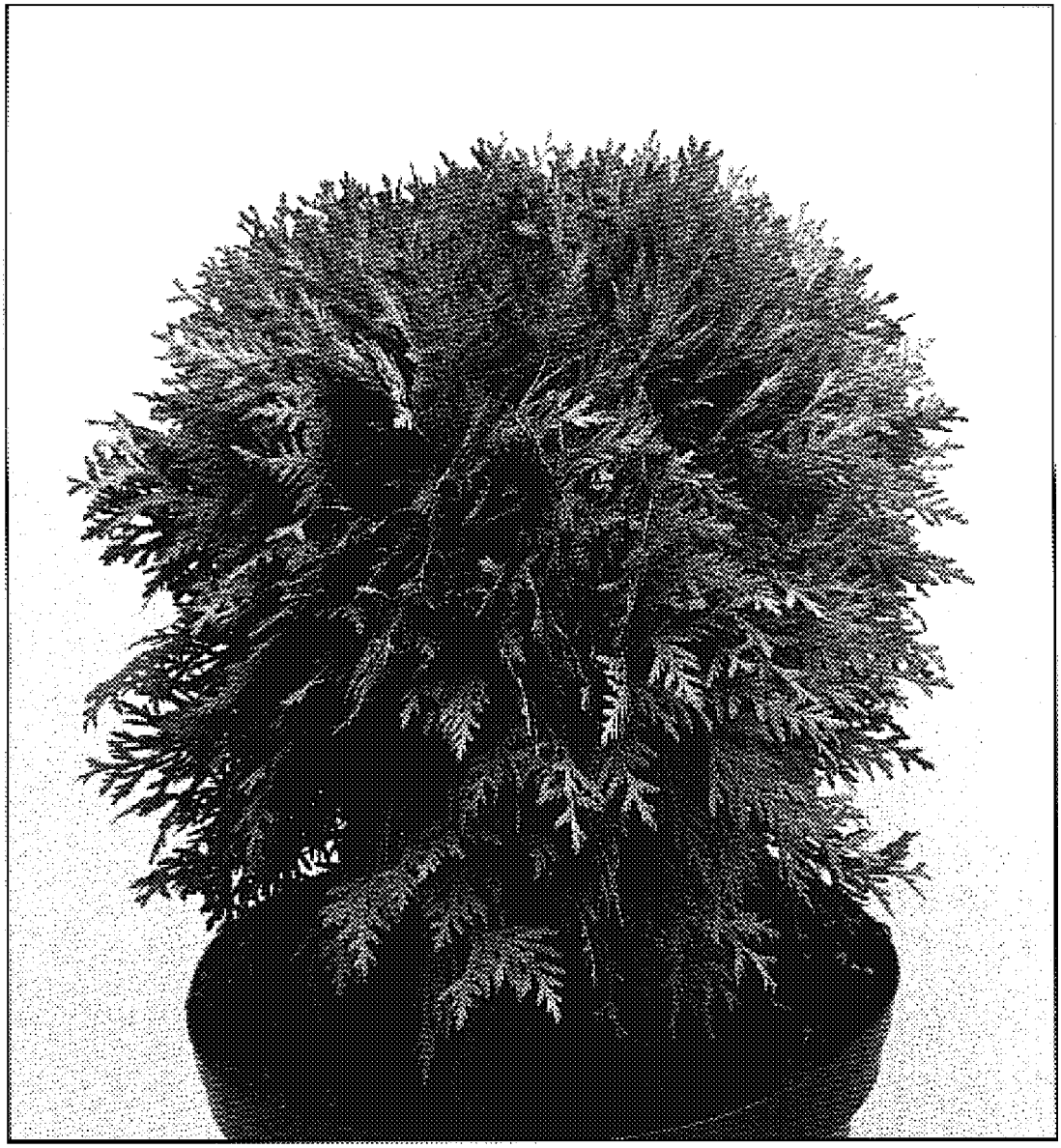

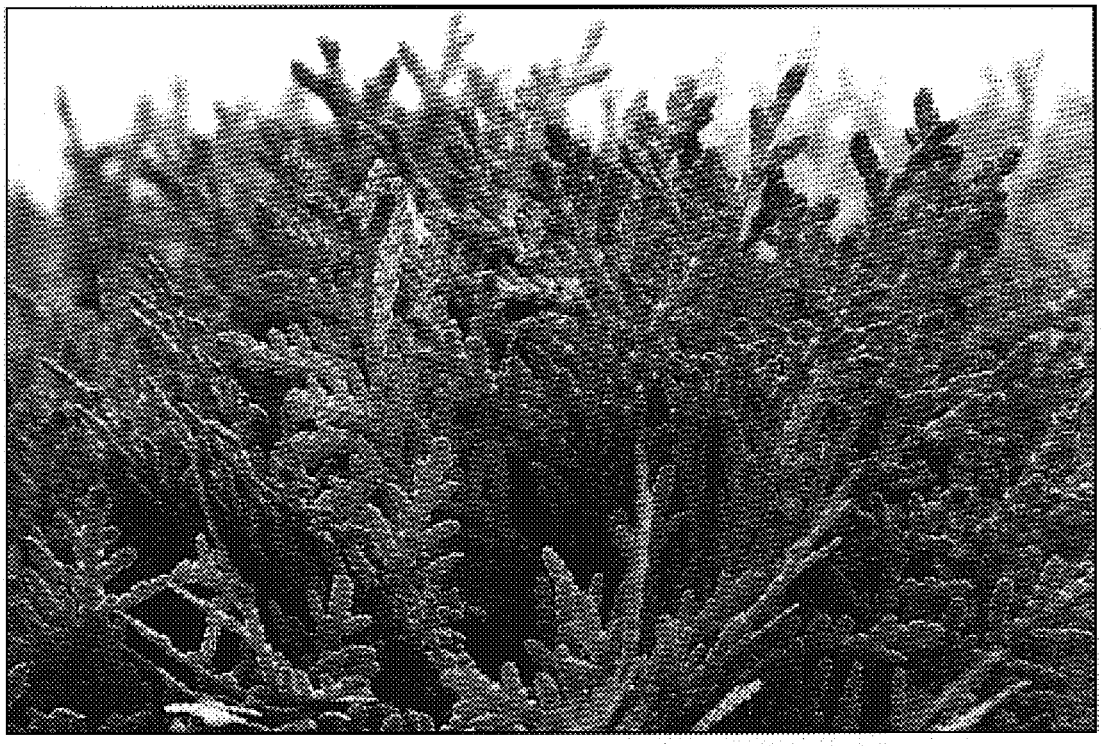

* * * * *